United States Patent [19]

Gagneux et al.

[11] 4,111,950
[45] Sep. 5, 1978

[54] TRIAZOLYL BENZOPHENONES

[75] Inventors: André Gagneux, Basel; Roland Heckendorn, Arlesheim; René Meier, Buus, all of Switzerland

[73] Assignee: Ciba-Geigy Corporation, Ardsley, N.Y.

[21] Appl. No.: 765,573

[22] Filed: Feb. 4, 1977

Related U.S. Application Data

[62] Division of Ser. No. 535,480, Dec. 23, 1974, Pat. No. 4,027,029, which is a division of Ser. No. 328,815, Jan. 31, 1973, Pat. No. 3,870,714.

[30] Foreign Application Priority Data

Feb. 7, 1972 [CH] Switzerland ..................... 1738/72
Aug. 31, 1972 [CH] Switzerland ..................... 12843/72
Nov. 3, 1972 [CH] Switzerland ..................... 16045/72

[51] Int. Cl.$^2$ ................. C07D 401/06; C07D 403/06; C07D 413/06; C07D 487/04
[52] U.S. Cl. ........................... 260/308 R; 260/293.69; 260/243.3; 544/132; 544/366
[58] Field of Search .......... 260/308 R, 268 C, 293.69, 260/326.5 CA, 247.5 E; 544/132

[56] References Cited

U.S. PATENT DOCUMENTS 3,852,300 12/1974 Gagneux et al. ............... 260/308 R
3,870,714 3/1975 Gagneux et al. ............... 260/308 R Primary Examiner—Alton D. Rollins
Attorney, Agent, or Firm—John J. Maitner

[57] ABSTRACT

Compounds of the class of 6-phenyl-4H-s-triazolo[1,5-a][1,4]benzodiazepine-2-carboxamides, their 5-oxides and their pharmaceutically acceptable acid addition salts have valuable pharmacological properties and are active ingredients for therapeutic compositions. In particular, these new compounds have an anti-convulsive and anti-aggressive action and inhibit somatic reflexes. Specific embodiments are N,N-dimethyl-6-phenyl-8-chloro-4H-s-triazolo[1,5-a][1,4]benzodiazepine-2-carboxamide, 6-(o-fluorophenyl)-8-chloro-4H-s-triazolo[1,5-a][1,4]benzodiazepine-2-carboxamide, N,N-dimethyl-6-(o-fluorophenyl)-8-chloro-4H-s-triazolo[1,5-a][1,4]benzodiazepine-2-carboxamide and N,N-dimethyl-6-(o-chlorophenyl)-8-chloro-4H-s-triazolo[1,5-a][1,4]benzodiazepine-2-carboxamide.

7 Claims, No Drawings

TRIAZOLYL BENZOPHENONES

CROSS-REFERENCE TO RELATED APPLICATIONS

This application is a division of copending application Ser. No. 535,480, filed Dec. 23, 1974, (now U.S. Pat. 4,027,029) which, in turn, is a division of application Ser. No. 328,815, filed Jan. 31, 1973 (now U.S. Pat. No. 3,870,714).

DETAILED DESCRIPTION

The present invention relates to new diazepine derivatives, to processes for their production, to therapeutic preparations containing the new compounds, and to the use thereof.

The diazepine derivatives according to the invention correspond to the general formula I

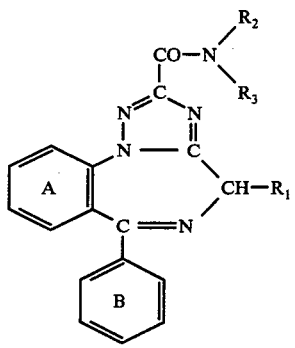

(I)

wherein
R$_1$ represents hydrogen, or an alkyl group having 1 to 3 carbon atoms, and
R$_2$ and R$_3$ independently of each other represent hydrogen, alkyl groups having 1 to 6 carbon atoms or hydroxyalkyl groups having 2 to 6 carbon atoms, dialkylaminoalkyl groups having in all 4 to 7 carbon atoms, or aralkyl groups having 7 to 9 carbon atoms, whereby, when R$_2$ and R$_3$ simultaneously represent alkyl groups as aforesaid, these alkyl groups may be either bound together direct or, in β- or γ- position, bound via an oxygen atom, the imino groups, a lower alkylimino hydroxyalkylimino group having at most 4 carbon atoms to form a bivalent radical having in all at most 10 carbon atoms, and
wherein each of the rings A and B independently of the other is unsubstituted or substituted by halogen up to atomic number 35, alkyl or alkoxy groups each having 1 to 6 carbon atoms, trifluoromethyl or nitro groups.

The invention also relates to the 5-oxides of the compounds of the general formula I, and to the addition salts of compounds of the general formula I with inorganic and organic acids.

In the compounds of the general formula I, R$_1$ as an alkyl group is, e.g. the ethyl or propyl group, and especially the methyl group; R$_2$ and R$_3$ as alkyl groups having 1 to 6 carbon atoms are, e.g. propyl, isopropyl, butyl, isobutyl, pentyl, isopentyl or hexyl groups, and preferably methyl groups or ethyl groups; as hydroxyalkyl groups having 2 to 6 carbon atoms they are, e.g. 2-hydroxypropyl, 3-hydroxypropyl, 2-hydroxybutyl, 3-hydroxybutyl, 2-hydroxy-1-methyl-propyl, 2-hydroxypentyl, 2-hydroxyhexyl and, in particular, 2-hydroxyethyl groups; as dialkylaminoalkyl groups having 4 to 7 carbon atoms they are, e.g. 2-(dimethylamino)-ethyl, 2-(dimethylamino)-propyl, 3-(dimethylamino)-propyl, 2-(diethylamino)-ethyl or 3-(diethylamino)-propyl groups; and as aralkyl groups having at most 7 to 9 carbon atoms they are, e.g. benzyl, phenethyl, α-, o-, m- or p-methylbenzyl, 3-phenylpropyl or α-methylphenethyl groups. With the exception of the lower alkyl groups, the aforementioned groups are present preferably only as R$_2$, together with hydrogen or a lower alkyl group as R$_3$.

Alkyl groups R$_2$ and R$_3$ bound together in the above defined manner form together with the adjacent nitrogen atom, i.e. as the grouping NR$_2$R$_3$, e.g. the 1-aziridinyl, 1-azetidinyl, 1-pyrrolidinyl, piperidino, hexahydro-1H-azepin-1-yl, morpholino, 1-piperazinyl or hexahydro-1H-1,4-diazepin-1-yl group. The two last-mentioned groups can be substituted in the 4-position, i.e. in the imino group, e.g. by a methyl, ethyl, propyl, isopropyl, butyl, isobutyl, 2-hydroxyethyl, 2-hydroxypropyl, 3-hydroxypropyl or 3-hydroxybutyl group, while all aforementioned rings can be substituted on carbon atoms by ethyl, propyl or, in particular, methyl groups. The following may be mentioned as examples of C-alkyl-substituted and C- and N-substituted radicals NR$_2$R$_3$ respectively: the 2-methyl-1-aziridinyl, 3,3-dimethyl-azetidinyl, 2,5-dimethyl-1-pyrrolidinyl, 2-methyl-, 3-methyl- and 4-methyl-piperidino, 2,6-dimethyl-piperidino, 2,4,6-trimethyl-piperidino, 2,2,6,6-tetramethyl-piperidino, 2,5-dimethyl-1-piperazinyl, 2,4,5-trimethyl-1-piperazinyl, 2,4,6-trimethyl-1-piperazinyl and 3,4,5-trimethyl-1-piperazinyl group.

Halogen atoms as substituents of rings A and B are fluorine, chlorine or bromine atoms; while alkyl groups and alkoxy groups having 1 to 6 carbon atoms are respectively, e.g. methyl, ethyl, propyl, isopropyl, butyl, isobutyl, tert.butyl, pentyl, isopentyl, 2,2-dimethyl-propyl, hexyl or isohexyl groups and methoxy, ethoxy, propoxy, isopropoxy, butoxy, isobutoxy, pentyloxy, isopentyloxy, 2,2-dimethylpropoxy, hexyloxy or isohexyloxy groups. Preferably, a substituent of ring A is fluorine, bromine, the trifluoromethyl group and, in particular, chlorine or the or the nitro group. Such a substituent is especially in the 8-position. Ring B is preferably unsubstituted, or substituted by fluorine, chlorine, bromine, the trifluoromethyl group or the nitro group in any desired position, particularly, however, by fluorine or chlorine in the o-position.

The compounds of the general formula I, their 5-oxides, and the corresponding addition salts with inorganic and organic acids possess valuable pharmacological properties. They have a central depressant action, particularly an anticonvulsive and anti-aggressive action, potentiate the action of anaesthetics and inhibit somatic reflexes. The anticonvulsive effectiveness can be shown, for example, in the pentetrazole-convulsion test on the mouse with oral doses of from ca. 0.1 mg/kg; and in the strychnine-convulsion test on the mouse with oral doses of frm ca. 1.0 mg/kg. In comparison to the pronounced pharmacological effects, the toxic effect of the compounds of the general formula I is negligible. In observation tests on various experimental animals, a high degree of sedation was observed with no, or only slight, lessening of the reaction to external stimuli. The central depressant, especially anticonvulsive, properties, as well as further properties, which can be determined by selected standard tests [cp. W. Theobald and H. A. Kunz, 'Arzneimittelforsch.' —, 122 (1963), and also W. Theobald et al., 'Arzneimittelforsch.' 17, 561 (1967], characterise the compounds of the general formula I and their 5-oxides, as well as their pharmaceutically acceptable addition salts with inorganic and organic acids, as active substances for tranquillisers, muscle relaxants and anticonvulsants, which can be used, e.g. for the treatment of states of agitation and tension, as well as for the treatment of epilepsy.

Of particular importance are compounds of the general formula I wherein $R_1$ is hydrogen or a methyl group, $R_2$ and $R_3$ denote hydrogen and/or lower alkyl groups, or together with the adjacent nitrogen atom they represent the 1-pyrrolidinyl, piperidino or 4-methyl-1-piperazinyl group, the ring A is unsubstituted, or preferbly substituted by a halogen atom up to atomic number 35, the nitro or trifluoromethyl group, and the ring B is either unsubstituted, or substituted by one of the substituents mentioned for ring A, whereby preferably at least one of the rings A and B carries one of the stated substituents. Particularly valuable compounds within the group are, on the one hand, compounds having one of the above mentioned substituents, especially the trifluoromethyl group and, in particular, a chlorine atom or the nitro group in ring A in the 8-position and, on the other hand, compounds having an unsubstituted ring B or one substituted in the ortho-position by fluorine or chlorine, and, in particular, those compounds which combine in themselves the stated substitution characteristics for rings A and B and, at the same time, contain hydrogen as $R_1$ and hydrogen and/or methyl or ethyl groups as $R_2$ and $R_3$, such as 6-phenyl-8-chloro-4H-s-triazolo [1,5-a][1,4]benzodiazepine-2-carboxamide, N,N-dimethyl- and N,N-diethyl-6-phenyl-8-chloro-4H-s-triazolo[1,5-a][1,4]benzodiazepine-2-carboxamide, and corresponding compounds having the 6-(o-fluorophenyl)- and 6-(o-chlorophenyl)-group instead of the 6-phenyl group, such as 6-(o-fluorophenyl)-8-chloro-4H-s- triazolo[1,5-a][1,4] benzodiazepine-2-carboxamide, N,N-dimethyl-6-(o-fluorophenyl)-8-chloro-4H-s-triazolo[1,5-a][1,4]benzodiazepine-2-carboxamide, N-methyl-, N-ethyl- and N,N-diethyl-6-(o-fluorophenyl)-8-chloro-4H-s-triazolo[1,5-a][1,4] benzodiazepine-2-carboxamide, 6-(o-chlorophenyl)-8-chloro-4H-s-triazolo[1,5-a][1,4]benzodiazepine-2-carboxamide, N-methyl-, N,N-dimethyl- and N,N-diethyl-6-(o-chlorophenyl)-8-chloro-4H-s-triazolo[1,5-a][1,4]benzodiazepine-2-carboxamide, as well as N,N-dimethyl-6-phenyl-8-nitro-4H-s-triazolo[1,5-a][1,4]benzodiazepine-2-carboxamide and N,N-dimethyl-6-phenyl-8-(trifluoromethyl)-4H-s-triazolo [1,5-a][1,4]benzodiazepine-2-carboxamide.

The compounds of the general formula I, their 5-oxides and their acid addition salts are produced according to the invention by a process in which a carboxylic acid of the general formula II

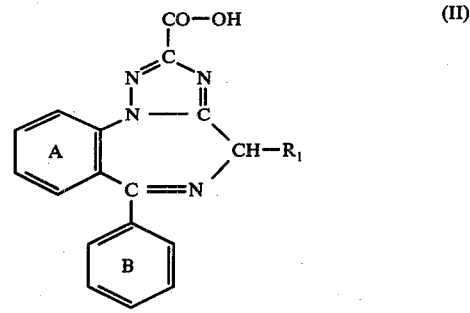

wherein $R_1$ has the meaning given under formula I, and the rings A and B can be substituted as defined under formula I, a reactive functional derivative of such a carboxylic acid, or the 5-oxide of such a compound, is reacted with a compound of the general formula III

wherein $R_2$ and $R_3$ have the meanings given under formula I, or with a reactive functional derivative of such a compound; and, optionally, the obtained reaction product oxidised to its 5-oxide, or, optionally, converted into an addition salt with an inorganic or organic acid. This process comprises, for example, the reaction of a carboxylic acid of the general formula II with a compound of the general formula III in the presence of a carbodiimide such as, e.g. dicyclohexyl-carbodiimide, in an inert solvent such as, e.g. tetrahydrofuran. Lower alkyl esters, such as, e.g. the methyl esters or ethyl esters of carboxylic acids of the general formula II, can be reacted in the cold state or, if necessary, by heating, possibly in a closed vessel, with compounds of the general formula III to give the corresponding amides of the general formula I. Moreover, it is possible also to convert amides of the general formula I, by heating them with compounds of the general formula III, into other amides embraced by the general formula I.

Further suitable reactive functional derivatives of carboxylic acids of the general formula II are the halides, particularly the chlorides, and anhydrides, especially the mixed anhydrides with carbonic acid semiesters. These functional derivatives are reacted with a compound of the general formula III, preferably in the presence of an acid-binding agent, e.g. of a strong tertiary organic base such as triethylamine, N-ethyl-diisopropylamine, pyridine or s-collidine, which in excess can also serve as the reaction medium, or in the presence of an excess of the reaction component of the general formula III in the presence or absence of an inert organic solvent, such as, e.g. dioxane, tetrahydrofuran, benzene or dimethylformamide. Further suitable derivatives of carboxylic acids of the general formula II are, e.g. their p-nitrophenyl esters and cyanomethyl esters, which are reacted with compounds of the general formula III in inert orgaic solvents, if necessary with heating. The 1-imidazolides of carboxylic acids of the general formula II are reacted with compounds of the general formula III under analogous conditions.

The isocyanates and isothiocyanates derived from compounds of the general formula III having a hydrogen atom as $R_3$ may be mentioned as applicable reactive functional derivatives of compounds of the general formula III which can be reacted direct with acids of the general formula II. The isocyanates and isothiocyanates are heated with the acids of the general formula II until the equimolar amount of carbon dioxide or carbon oxysulphide is liberated. The reactions with isocyanates and isothiocyanates can be performed in the presence or absence of an inert organic solvent having a sufficiently high boiling point or boiling range. Further reactive functional derivatives to be mentioned of compounds of the general formula III having a hydrogen atom as $R_3$ are, e.g. the N-trimethylsilyl derivatives obtainable by reaction of these amines with trimethylsilyl chloride in inert, anhydrous, organic solvents; the N-trimethylsilyl derivatives react with reactive functional derivatives of the acids of the general formula II in inert organic solvents to give N-trimethylsilyl derivatives of amides of the general formula I, from which the desired amides are obtained by decomposition with water or with lower alkanols.

As functional derivatives of such compounds of the general formula III wherein neither $R_2$ nor $R_3$ is a hydrogen atom, their N-chlorocarbonyl derivatives, for example, are reacted with salts (e.g. alkali salts) of carboxylic acids of the general formula II, in the presence or absence of inert organic solvents, and the reaction mixtures heated until the equimolar amount of carbon dioxide has been liberated from the primarily formed carboxylic acid-carbamic acid anhydrides. Similarly, from compounds of the general formula III having radicals $R_2$ and $R_3$ which are not hydrogen, it is possible to derive sulphurous acid-monoalkyl ester amides and phosphorous acid-o-phenylenediester-amides, which, on reaction with carboxylic acids of the general formula II in organic solvents, such as, e.g. pyridine, dioxane or dimethylformamide or benzene, yield the desired amides of the general formula I.

The production of the carboxylic acids of the general formula II and their reactive functional derivatives is described later on in the text. The compounds of the general formula III and reactive derivatives thereof are known in considerable numbers, and others can be produced in a manner analogous to that for the known ones.

According to a second process for the production of the compounds of the general formula I, their 5-oxides and their acid addition salts, a reactive ester of a compound of the general formula IV

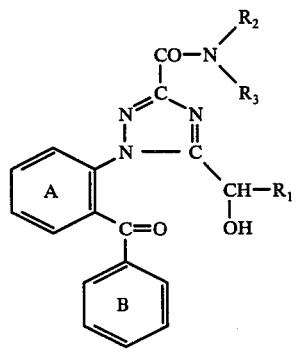

(IV)

wherein $R_1$, $R_2$ and $R_3$ have the meanings given under formula I, and the rings A and B can be substituted as defined under formula I, is reacted with ammonia or with hexamethylenetetramine; and, optionally, the obtained reaction product of the general formula I oxidised to its 5-oxide; or, optionally, converted into an addition salt with an inorganic or organic acid. By virtue of the reaction according to the process, the reactive ester group is replaced by the amino group; and, simultaneously, ring closure effected with elimination of water. The reaction is performed at room temperature or at moderately elevated temperatures, i.e. preferably between 20° and 100°, in an inert organic solvent. The ammonia can be used as such or in the form of the concentrated aqueous solution, preferably in appreciable excess; and the employed inert organic solvent is, for example, dioxane, tetrahydrofuran, ethanol, butanol or, with the use of anhydrous ammonia, e.g. also benzene or toluene. Suitable reactive esters of compounds of the general formula IV, the production of which is described later on in the text, are, e.g., the chlorides, and particularly the iodides produced in situ from these, preferably immediately before the reaction with ammonia.

In a third, and with the second related, process for the production of the compounds of the general formula I, a compound of the general formula V

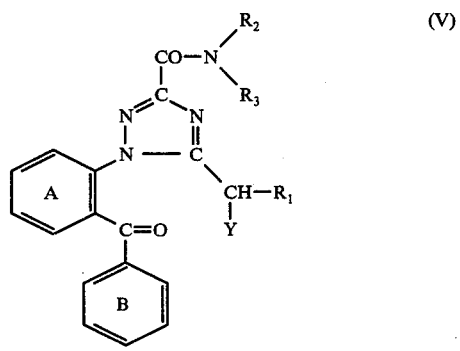

(V)

wherein
Y represents the amino group, or a nitrogen-containing group convertible in situ into the amino group by reduction or solvolysis,
$R_1$, $R_2$ and $R_3$ have the meanings given under formula I, and the rings A and B can be substituted as defined under formula I,
is cyclised, or subjected to a reduction or solvolysis under cyclising conditions; and, optionally, the obtained reaction product of the general formula I oxidised to its 5-oxide; or, optionally, converted into a addition salt with an inorganic or organic acid.

The cyclisation of compounds of the general formula V wherein Y is a free amino group can be performed in the presence or absence of a condensation agent, and preferably in a solvent. Suitable condensation agents are, for example, tertiary organic bases such as pyridine or triethylamine, and also, e.g. sulphonic acids such as o- or p-toluenesulphonic acid. Suitable solvents are, in particular, polar solvents, such as, e.g. lower alkanols. Cyclisation is preferably performed at 50°–120° C, in a closed vessel if necessary.

A group Y convertible by reduction into the amino group is especially the azido group. It is possible to use, for example, triphenylphosphine for the reduction and simultaneous cyclisation of azido compounds embraced by the general formula V. It is allowed to react preferably at room temperature or at moderately elevated temperature, i.e. between ca. 20° and 100° C, in an inert organic solvent such as, e.g. tetrahydrofuran, dioxane or benzene. With evolution of nitrogen, there is formed from the azido group firstly an N-(triphenylphosphoranylidene)-amino group, which reacts immediately with the keto group with ring closure and formation of the corresponding compound of the general formula I. Triphenylphosphine oxide is liberated in the process; the overall reaction can hence be considered as being a reduction. A further suitable reducing agent is tin(II)-chloride, which is used, e.g. in low-alkanolic-aqueous, particularly ethanolic-aqueous alkali solution, especially sodium hydroxide solution, at temperatures of between ca. 0° and the boiling temperature. Also applicable is the action of hydrogen in the presence of a hydrogenation catalyst, e.g. of a palladium charcoal catalyst, platinum oxide or Raney nickel, in an organic solvent such as dioxane, ethanol, methanol or tetrahydrofuran, at normal pressure and at moderately elevated temperature.

Examples of radicals Y convertible by solvolysis into the amino group are acylamides, diacylamides and, in particular, the phthalimido group. Solvolysis and simultaneous cyclisation of compounds of the general formula V wherein Y is a phthalimido group can be performed particularly with hydrazine, employed, e.g. as hydrate, in a lower alkanol such as methanol or ethanol, to which is added, to effect an improvement of dissolving power, preferably a halogenated hydrocarbon such as chloroform, at room temperature to the boiling temperature of the reaction mixture, preferably at between ca. 20° and 60° C.

The production of the starting materials of the general formula V is described later on in the text.

According to a fourth process likewise for the production of compounds of the general formula I, their 5-oxides and their acid addition salts, a aldehyde of the general formula VI

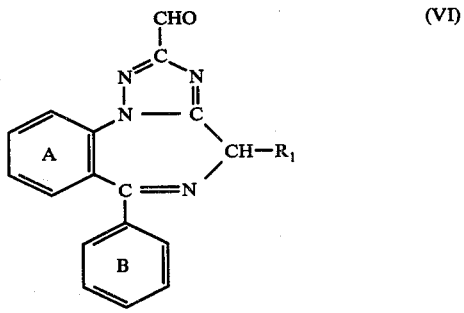

(VI)

wherein $R_1$ has the meaning given under formula I, and the rings A and B can be substituted as defined there, is reacted with a compound of the earlier given general formula III, wherein $R_2$ and $R_3$ have the meanings given under formula I, in the presence of an alkali metal cyanide and a selective oxidising agent; and, optionally, the obtained reaction product oxidised to its 5-oxide; or, optionally, converted into an addition salt with an inorganic or organic acid. The alkali metal cyanide employed is, for example, potassium cyanide and, in particular, sodium cyanide. By selective oxidising agents are meant those which do not attack under the reaction conditions the aldehyde group of the starting material of formula VI, but which are able to oxidise the hydroxymethylene group of the intermediately formed cyanohydrin to the carbonyl group. Manganese dioxide is a suitable oxidising agent, particularly in the active form described by J. Attenburrow et al., J. Chem.Soc. 1952, 1104. The reactions with manganese dioxide are performed preferably in isopropanol, or in another lower secondary alkanol to which can be added a further organic solvent inert under the reaction conditions, preferably one having a good dissolving capacity for the starting materials of the general formula VI, such as, for example, dioxane, the said reactions being performed in the cold state, e.g. between $-10°$ C and $+10°$ C, preferably around 0° C. Relative to the amount of compound of the general formula VI, there is used, for example, an appreciable excess of the compound of the general formula III, and also of the alkali metal cyanide, e.g. the ca. 5-fold molar amount of the latter, and a still greater excess, e.g. the ca. 20-fold molar amount of manganese dioxide, with a reaction duration of 2 to 6 hours, preferably ca. 4 hours.

The conversion of the obtained compounds of the general formula I into their 5-oxides, or into their acid addition salts, is described more fully later on in the text.

The aldehydes of the general formula VI required as starting materials are, for their part, new compounds. They can be obtained, for example, from lower alkyl esters of carboxylic acids of the general formula II, the production of which is described at a later stage, either in two steps by reduction of the stated esters by means of lithium aluminium hydride in an ethereal solvent such as tetrahydrofuran, at temperatures around 0° C, and a careful oxidation of the obtained hydroxymethyl compounds, e.g. by means of manganese dioxide in benzene at its boiling temperature, or direct by reduction of the said esters by means of sodium-bis-(ethoxymethoxy)-aluminium hydride in abs. toluene.

Suitable oxidising agents for the conversion (optionally following the aforementioned production processes) of compounds of the general formula I into their 5-oxides are preferably hydrogen peroxide or peroxy acids at a temperature of ca. 0° to 70° C. Suitable peroxy acids are, e.g. peroxyacetic acid, or peroxybenzoic acids, such as peroxybenzoic acid or, in particular, m-chloroperoxybenzoic acid. The oxidising agents are preferably used in a solvent, e.g. peroxyacetic acid in acetic acid and peroxybenzoic acid in halogenated hydrocarbons such as methylene chloride or chloroform.

The formation of the acid addition salts is described later on in the text.

The present invention includes also modifications of the aforementioned processes; where, for example, a process is interrupted at some stage, or where a compound occurring as an intermediate at a certain stage is taken as the starting material and processed through the remaining stages, or where a starting material is formed under the reaction conditions, or is used in the form of a salt. Instead of racemates of optically active compounds, it is possible to use as starting materials also single optical antipodes, or, where diastereomery is present, a specific racemate. Such starting materials too can be optionally used in the form of salts.

The starting materials of the general formula II for the first mentioned process for the production of the compounds of the general formula I are obtained, for example, as follows:

The starting materials are compounds of the general formula VI:

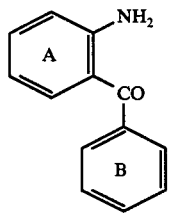 (VI)

wherein the rings A and B can be substituted as defined under formula I. Such compounds are described in the literature: e.g. 2-amino-5-chlorobenzophenone [cp. F.D. Chattaway, J. Chem. Soc. 85, 344 (1904)], 2-amino-2', 5-dichloroacetophenone [cp. L. H. Sternbach et al., J. Org. Chem. 26, 4488 (1961)], as well as 2-amino-5-chloro-2'-fluorobenzophenone and others [cp. L. H. Sternbach et al., J.Org.Chem. 27, 3781–3788 (1962)]. The compounds of the general formula VI are diazotised, and subsequently the obtained diazonium salts coupled with (2-chloroalkaneamido)-malonic acid diethyl esters, of which the chloroalkaneamido group contains at most 5 carbon atoms, such as, e.g. (2-chloroacetamido)-malonic acid diethyl ester [cp. Ajay Kumar Bose, J.Indian Chem.Soc. 31, 108–110 (1954)], to give the corresponding (2-chloroalkaneamido)-(2-benzoyl-phenylazo)-malonic acid diethyl esters. The coupling products are then converted by the successive action of sodium hydroxide and hydrochloric acid into the compounds of the general formula VII

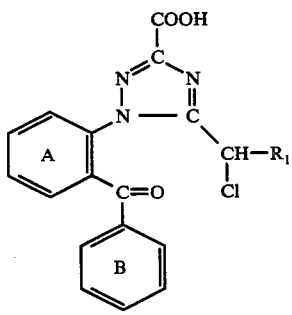 (VII)

wherein $R_1$ has the meaning given under formula I, and the rings A and B can be substituted as defined under formula I. These compounds are reacted analogously to the second-mentioned process for the production of the compounds of the general formula I, preferably after pretreatment with potassium iodide, with aqueous ammonia or also with hexamethylene tetramine, whereby the chlorine or iodine atom is replaced by the amino group, and simultaneously, with elimination of water, ring closure to form the carboxylic acids of the general formula II effected. It is also possible to react the compounds of the general formula IX, after pretreatment with potassium iodide, firstly with sodium azide to give compounds of the general formula VIII:

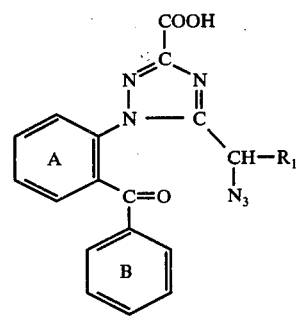 (VIII)

wherein $R_1$ has the meaning given under formula I, and the rings A and B can be substituted as defined under formula I. The compounds of the general formula VIII are thereupon cyclised, analogously to the third-mentioned process for the production of the compounds of the general formula I, with triphenylphosphine, with the evolution of nitrogen, to give carboxylic acids of the general formula II.

According to a variant of the above reaction sequence which is particularly advantageous for the production of carboxylic acids of the general formula II having a halogen atom as substituent of ring B, or of their lower alkyl esters, sodium hydroxide is allowed to act on the above mentioned (2-chloroalkaneamido)-(2-benzoylphenylazo)-malonic acid-diethyl esters, of which the benzoyl radical and phenyl radical can carry the substituents given for the rings B and A, respectively, the reaction being performed under mild conditions, i.e. with application of at most the double-molar amount of sodium hydroxide in highly diluted organic-aqueous solution at ca. 10° C to room temperature; and the reaction mixture neutralised before processing. In this manner there are obtained, instead of the carboxylic acids of the general formula VII, their ethyl esters of the general formula VIIa

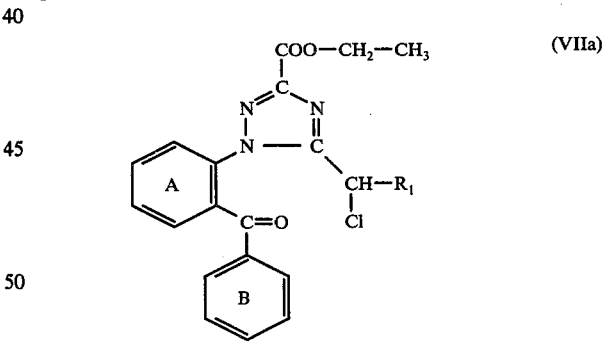 (VIIa)

wherein R has the meaning given under formula I, and the rings A and B can be substituted as defined under formula I. The ethyl esters of the general formula VIIa can be converted, in the same way as the corresponding carboxylic acids of the general formula VII, by ring closure reactions analogously to the first-mentioned process for the production of compounds of the general formula I, e.g. by reaction with ammonia or preferably with hexamethylenetetramine, into the ethyl esters of carboxylic acids of the general formula II, and these hydrolised to the free carboxylic acids, or used direct as starting materials in the first-mentioned process for the production of compounds of the general formula I.

Furthermore, the above mentioned (2-chloroalkaneamido)-(2-benzoyl-phenylazo)-malonic acid dimethyl esters, of which the benzoyl radical and phenyl radical can carry substituents given for the ring B and A, respectively, can be reacted also with ammonia in aqueous-organic solution, e.g. with a mixture of conc. aqueous ammonia and dimethylformamide. The ethyl ester of the corresponding compound of the general formula VII can be obtained under mild conditions and with a low ammonia concentration; but the reaction conditions can also be adjusted in such a manner that also the aliphatically bound chlorine atom reacts in situ with ammonia, and the second ring closure to the ethyl ester of the corresponding carboxylic acid of the general formula II occurs. Optionally, it is possible finally, by a further lengthening of the reaction time and/or a higher ammonia concentration, as well as, if necessary, a raising of the temperature, to effect also the ammonolysis of the esters of carboxylic acids of the general formula II formed on ring closure to give N-unsubstituted amides of the general formula I according to the first-mentioned production process for these compounds.

Instead of (2-chloroalkaneamido)-2-benzoylphenylazo)-malonic acid diethylesters, it is possible to use for the aforementioned reaction sequences other lower dialkyl esters; for example, particularly for the last-mentioned variant with subsequent ammonolysis in situ, the dimethyl esters. It is also possible, especially in the case of the variant comprising the formation of the triazole ring and subsequent ring closure in situ for the formation of the diazepine ring by means of ammonia solutions, to use (2-bromoalkaneamido)-compounds in place of (2-chloroalkaneamido)-compounds.

Optionally, reactive functional derivatives are produced in the usual manner from the carboxylic acids of the general formula II. For example, there are obtained, by the action of excess thionyl chloride at its boiling temperature and removal of the excess of thionyl chloride in vacuo, the chlorides of carboxylic acids of the general formula II, mostly as mixtures with their hydrochlorides. These mixtures are preferably reacted direct with an increased excess—corresponding to the hydrogen chloride present—of compounds of the general formula III. Lower alkyl esters of carboxylic acids of the general formula II are obtained, for example, by the boiling of the carboxylic acids in the lower alkanols saturated with hydrogen chloride which are desired as the ester component. Also obtained are, for example, mixed anhydrides with alkoxyformic acids by the reaction, in the cold state, of the carboxylic acids of the general formula II with lower chloroformic acid alkyl esters, in the presence of an acid-binding agent such as triethylamine, in an inert solvent such as tetrahydrofuran. For the production of the 1-imidazolidines of the carboxylic acids of the general formula II, the latter are, for example, allowed to act at room temperature, or at slightly elevated temperature, on 1,1-carbonyldiimidazole until the evolution of carbon dioxide has ceased. The p-nitrophenyl esters are obtained, for example, by the reaction, in the cold state, of carboxylic acids of the general formula II with p-nitrophenol, in the presence of N,N'-dicyclohexyl-carbodiimide, in an inert solvent such as tetrahydrofuran.

Starting materials of the general formula IV for the second-mentioned process for the production of compounds of the general formula I are obtained, for example, by the conversion of compounds of the general formula VII by boiling with excess thionyl chloride into their acid chlorides; and the reaction of the last-mentioned with at least the double-molar amount, preferably, however, with an appreciable excess, of a compound of the general formula III in an inert organic solvent such as, e.g. chloroform or methylene chloride; and, optionally, the subsequent replacement of the chlorine atom present in place of the hydroxyl group by a methanesulphonyloxy- or p-toluenesulphonyloxy group, e.g. by reaction with the sodium salt of methanesulphonic acid or p-toluenesulphonic acid, also by bromine, e.g. by means of potassium bromide, or, preferably immediately before the reaction according to the invention with ammonia, by iodine, by means of potassium iodide.

The starting materials of the general formula V having an amino group as the radical Y for the third-mentioned process for the production of compounds of the general formula I are obtained, e.g., by reaction of reactive esters of compounds of the general formula IV, particularly of the iodides produced in situ from the chlorides by means of potassium iodide, with ammonia under mild conditions, preferably at ca. $0°-5°$ C in an inert organic solvent, such as, e.g. dimethylformamide, methanol or ethanol. Together with the subsequent cyclisation according to the invention, i.e with the third-mentioned process for the production of compounds of the general formula I, the above described reaction thus forms a two-stage variant of the second-mentioned process for the production of compounds of the general formula I.

Starting materials of the general formula V having an azido group as the radical Y are obtained, for example, by an analogous reaction of reactive esters of compounds of the general formula II with sodium or potassium azide in an inert organic solvent such as, e.g. dimethylsulphoxide.

For the production of compounds of the general formula V having a radical Y convertible by solvolysis into the ammonia group, such as, e.g. an acylamido, diacylamido or, in particular, the phthalimido group, it is likewise possible to commence with reactive esters of compounds of the general formula IV, and to react these with alkali metal derivatives of amides or imides, such as, e.g. with phthalamide-potassium. However, such compounds can also be obtained by a process in which firstly the above mentioned diazonium salts of compounds of the general formula VI are coupled with (2-acylamidoalkaneamido)-, (2-diacylimidoalkaneamido- or (2-phthalimido-alkaneamido)-malonic acid diethyl esters, particularly with (2-phthalimido-acetamido)-malonic acid diethyl esters, instead of with (2-chloroalkaneamido)-malonic acid diethyl esters, and the coupling products converted by the successive action of sodium hydroxide and hydrochloric acid into analogues to compounds of the general formula VII, which carry, instead of a chlorine atom, an acylamido, diacylimido or, in particular, a phthalimido group. The carboxamides embraced by the general formula V are subsequently produced from these carboxylic acids in one or preferably two stages, that is, e.g., by way of the carboxylic acid chloride or the lower alkyl esters, analogously to the first-mentioned process for the production of compounds of the general formula I, and also analogous to the production of reactive esters of compounds of the general formula IV.

The compounds of the general formula I obtained by the processes according to the invention are optionally converted, in the usual manner, into their addition salts with inorganic and organic acids. For salt formation, for example, it is possible to use hydrochloric acid, hydrobromic acid, sulphuric acid, phosphoric acid, perchloric acid, methane sulphonic acid, ethane sulphonic acid or citric acid, preferably in the presence of a solvent such as, e.g. acetone, methanol, ethanol, ether, or mixtures thereof.

The compounds of the general formula I, as well as their 5-oxides and the corresponding, pharmaceutically acceptable acid addition salts, are preferably administered orally or rectally. The daily doses vary between 0.01 and 2 mg/kg for warm-blooded animals. Suitable dosage units, such as dragées, tablets or suppositories, preferably contain 0.5–25 mg of an active substance according to the invention, i.e. of a compound of the general formula I, of its 5-oxide, or of a pharmaceutically acceptable acid addition salt of these substances. The said dosage units are produced by the combination of the active substance with solid pulverulent carriers such as lactose, saccharose, sorbitol, mannitol; starches such as potato starch, maize starch or amylopectin, also laminaria powder or citrus pulp powder; cellulose derivatives or gelatine, optionally with the addition of lubricants such as magnesium or calcium stearate, or polyethylene glycols, to form tablets or dragée cores. The latter are coated, for example, with concentrated sugar solutions which may also contain, e.g. gum arabic, talcum and/or titanium dioxide; or with a lacquer dissolved in readily volatile organic solvents or solvent mixtures. Dyestuffs can be added to these coatings; e.g., for identification of the various doses of active substance. Further suitable oral dosage units are hard gelatine capsules, as well as soft closed capsules from gelatine and a softener such as glycerin. The hard capsules contain the active substance preferably as a granulate in admixture with lubricants such as talcum or magnesium stearate, and, optionally, stabilisers such as sodium metabisulphite or ascorbic acid.

The following directions further illustrate the preparation of tablets, dragees and suppositories.

(a) An amount of 50.0 g of N,N-dimethyl-6-phenyl-8-chloro-4H-s-triazolo[1,5-a][1,4]benzodiazepine-2-carboxamide is mixed with 500 g of lactose and 292 g of potato starch; the mixture is then moistened with an alcoholic solution of 8 g of gelatine, and granulated through a sieve. After the granulate has dried, 60 g of potato starch, 60 g of talcum, 10 g of magnesium stearate and 20 g of highly-dispersed silicon dioxide are mixed in, and the mixture is pressed to form 10,000 tablets each weighing 105 mg and each containing 5 mg of active substance; the tablets can optionally be provided with grooves for a more precise adjustment of the storage amount.

(b) An amount of 1.0 g of N,N-dimethyl-6-(o-fluorophenyl)-8-chloro-4H-s-triazolo[1,5-a][1,4]benzodiazepine-2-carboxamide is well mixed with 16 g of maize starch and 6 g of highly-dispersed silicon dioxide. The mixture is moistened with a solution of 2 g of stearic acid, 6 g of ethylcellulose and 6 g of stearin in ca. 70 ml of isopropyl alcohol, and granulated through a sieve III (Ph. Helv. V). The granulate is dried for ca. 14 hours, and then put through sieve III–IIIa. It is thereupon mixed with 16 g of maize starch, 16 g of talcum and 2 g of magnesium stearate, and the whole pressed to form 1000 dragée cores. These are coated with a concentrated syrup of 2 g of lacca, 7.5 g of gum arabic, 0.15 g of dyestuff, 2 g of highly dispersed silicon dioxide, 25 g of talcum and 53.35 g of sugar, and then dried. The obtained dragées each weigh 161.0 mg and each contain 1.0 mg of active substance.

(c) 5.0 g of N,N-diethyl-6-phenyl-8-chloro-4H-s-triazolo [1,5-a][1,4]benzodiazepine-2-carboxamide and 1995 g of finely ground suppository foundation substance (e.g. cocoa butter) are thoroughly mixed and then melted. The obtained melt, maintained homogeneous by stirring, is used to pour 1000 suppositories each of 2 g. They each contain 5 mg of active substance.

It is equally advantageous to use as active substance for tablets, dragées and suppositories the same amounts of N,N-diethyl-6-(o-fluorophenyl)-8-chloro-4H-s-triazolo [1,5-a][1,4]benzodiazepine-2-carboxamide or N,N-diethyl-6-(o-chlorophenyl)-8-chloro-4H-s-triazolo[1,5-a][1,4]benzodiazepine-2-carboxamide.

The following examples further illustrate the production of the new compounds of the general formula I, as well as of starting materials not hitherto known; the given examples, however, are not intended in any way to limit the scope of the invention. The temperatures are expressed in degrees Centigrade.

EXAMPLE 1

An amount of 5.08 g (0.015 mole) of 6-phenyl-8-chloro-4H-s-triazolo[1,5-a][1,4]benzodiazepine-2-carboxylic acid is refluxed with 50 ml of thionyl chloride for 1 hour. The clear yellow solution is concentrated at 40° in vacuo, and the residue again dissolved, to effect the total removal of the thionyl chloride, in 100 ml of abs. toluene, and the solution again concentrated by evaporation.

A solution of 22 g (0.3 mole) of diethylamine in 100 ml of abs. dioxane is poured over the obtained crude mixture of 6-phenyl-8-chloro-4H-s-triazolo[1,5-a][1,4]benzodiazepine-2-carbonyl chloride and its hydrochloride, and the whole refluxed for 1 hour. The reaction mixture is then concentrated at 40° in vacuo, and the residue dissolved in a mixture of 250 ml of chloroform and 100 ml of water. The organic phase is washed twice with 100 ml of water each time, dried over sodium sulphate, and concentrated at 40° in vacuo. The residue is crystallised from benzene/hexane to obtain, after drying in vacuum, N,N-diethyl-6-phenyl-8-chloro-4H-s-triazolo[1,5-a][1,4]benzodiazepine-2-carboxamide, M.P. 175°–177°.

The final materials listed on the following page are obtained in an analogous manner with use of the stated amines instead of the diethylamine.

with 13.5 g (0.3 mole) of dimethylamine: N,N-dimethyl-6-phenyl-8-chloro-4H-s-triazolo[1,5-a][1,4]benzodiazepine-2carboxamide, M.P. 135°–137° (from methylene chloride/hexane);

with 9.3 g (0.3 mole) of methylamine: N-methyl-6-phenyl-8-chloro-4H-s-triazolo[1,5-a][1,4]benzodiazepine-2-carboxamide;

with 13.5 g (0.3 mole) of ethylamine: N-ethyl-6-phenyl-8-chloro-4H-s-triazolo[1,5-a][1,4]benzodiazepine-2-carboxamide;

with 18 g (0.3 mole) of isopropylamine: N-isopropyl-6-phenyl-8-chloro-4H-s-triazolo[1,5-a][1,4]benzodiazepine-2-carboxamide;

with 21.3 g (0.3 mole) of pyrrolidine: 1-[(6-phenyl-8-chloro-4H-s-triazolo[1,5-a][1,4]benzodiazepin-2-yl)carbonyl]-pyrrolidine;

with 25.5 g (0.3 mole) of piperidine: 1-[(6-phenyl-8-chloro-4H-s-triazolo[1,5-a][1,4]benzodiazepin-2-yl)carbonyl]-piperidine;

with 26 g (0.3 mole) of morpholine: 4-[(6-phenyl-8-chloro-4H-s-triazolo[1,5-a][1,4]benzodiazepin-2-yl)carbonyl]-morpholine;

with 15 g (0.15 mole) of 1-methyl-piperazine and use of 250 ml of methylene chloride and 100 ml of 0.1 N sodium hydroxide solution instead of chloroform/water to dissolve the evaporation residue of the reaction mixture: 1-[(6-phenyl-8-chloro-4H-s-triazolo[1,5-a][1,4]benzodiazepin-2-yl)-carbonyl]-4-methyl-piperazine.

The corresponding amides are likewise obtained in an analogous manner, by use of the below stated amounts (corresponding in each case to 0.015 mole) of substituted 6-phenyl-4H-s-triazolo[1,5-a][1,4]benzodiazepine-2-carboxylic acids and 22 g (0.3 mole) of diethylamine and 13.5 g (0.3 mole) of dimethylamine, respectively:

starting with 5.60 g of 6-(o-chlorophenyl)-8-chloro-4H-s-triazolo[1,5-a][1,4]benzodiazepine-2-carboxylic acid: N,N-diethyl-6-(o-chlorophenyl)-8-chloro-4H-s-triazolo[1,5-a][1,4]benzodiazepine-2-carboxamide, M.P. 156°–158° (from isopropanol), and N,N-dimethyl-6-(o-chlorophenyl)-8-chloro-4H-s-triazolo[1,5-a][1,4]benzodiazepine-2-carboxamide, M.P. 142°–145° (from isopropanol);

starting with 5.35 g of 6-(o-fluorophenyl)-8-chloro-4H-s-triazolo[1,5-a][1,4]benzodiazepine-2-carboxylic acid: N,N-diethyl-6-(o-fluorophenyl)-8-chloro-4H-s-triazolo [1,5-a][1,4]benzodiazepine-2-carboxamide, M.P. 200°–202° (from isopropanol), and N,N-dimethyl-6-(o-fluorophenyl)-8-chloro-4H-s-triazolo[1,5-a][1,4]benzodiazepine-2-carboxamide, M.P. 180°–182° (from isopropanol);

starting with 6.10 g of 6-($\alpha,\alpha,\alpha$-trifluoro-o-tolyl)-8-chloro-4H-s-triazolo[1,5-a][1,4]benzodiazepine-2-carboxylic acid: N,N-diethyl- and N,N-dimethyl-6-($\alpha,\alpha,\alpha$-trifluoro-o-tolyl)-8-chloro-4H-s-triazolo[1,5-a][1,4]benzodiazepine-2-carboxamide;

starting with 4.83 g of 6-phenyl-8-fluoro-4H-s-triazolo [1,5-a][1,4]benzodiazepine-2-carboxylic acid: N,N-diethyl- and N,N-dimethyl-6-phenyl-8-fluoro-4H-s-triazolo[1,5-a][1,4]benzodiazepine-2-carboxamide;

starting with 5.75 g of 6-phenyl-8-bromo-4H-s-triazolo[1,5-a][1,4]benzodiazepine-2-carboxylic acid: N,N-diethyl- and N,N-dimethyl-6-phenyl-8-bromo-4H-s-triazolo[1,5-a][1,4]benzodiazepine-2-carboxamide.

6-Phenyl-8-chloro-4H-s-triazolo[1,5-a][1,4]benzodiazepine-2-carboxylic acid is produced as follows:

(a) A solution of 58.0 g (0.25 mole) of 2-amino-5-chlorobenzophenone [cp. F. D. Chattaway, J. Chem. Soc. 85, 344 (1904)] in 310 ml of glacial acetic acid/conc. hydrochloric acid (4:1) is diazotised at room temperature, with stirring, with 50 ml (0.25 mole) of aqueous sodium nitrite solution. Additions are made to the obtained diazonium salt solution of 150 g of ice and, quickly dropwise, a solution of 52.4 g (0.208 mole) of (2-chloroacetamido)malonic acid diethyl ester [cp. Ajay Kumar Bose, J. Indian Chem. Soc. 31, 108–110 (1954)] in 600 ml of acetone. There is then added dropwise at 5°–10°, in the course of 20 minutes, a solution of 276.0 g (2 moles) of potassium carbonate in 500 ml of water; stirring is continued for a further hour and benzene and saturated sodium chloride solution subsequently added. The benzene solution is separated, washed with saturated sodium chloride solution, dried over sodium sulphate, and concentrated by evaporation. There is thus obtained 121 g of crude (2-chloroacetamido)(2-benzoyl-4-chlorophenylazo)-malonic acid diethyl ester.

(b) The crude diethyl ester obtained according to (a) is dissolved in 1.5 liters of dioxane. An amount of 36 g (0.9 mole) sodium hydroxide dissolved in 2 liters of water is added to the obtained dioxane solution; the mixture is stirred for 30 minutes, and the dioxane then evaporated off in vacuo. The residue is diluted with 500 ml of water; 20 g of active charcoal is added, the mixture well stirred, and filtered through purified diatomaceous earth. 2N Hydrochloric acid is added to the filtrate, with thorough stirring, until an acid reaction to a congo-red indicator is obtained; the precipitated carboxylic acid is filtered off under suction, subsequently washed with water, and recrystallised from hot methanol. The obtained 1-(2-benzoyl-4-chlorophenyl)-5-(chloromethyl)-1H-1,2,4,-triazole-3-carboxylic acid sinters at 137°–138° and melts, with decomposition, at 169°–171°. The crystals contain an equimolar amount of methanol.

The following are obtained analogously to (a) and (b):

with the use of 66.5 g (0.25 mole) of 2-amino-2',5-dichlorobenzophenone: 1-[2-(o-chlorobenzoyl)-4-chlorophenyl]-5-(chloromethyl)-1H-1,2,4-triazole-3-carboxylic acid, M.P. 170°–175° (decomposition); substance precipitated from solution in aqueous ammonia with 2N hydrochloric acid);

with the use of 62.5 g (0.25 mole) of 2-amino-5-chloro-2'-fluorobenzophenone: 1-[2-(o-fluorobenzoyl)-4-chlorophenyl]-5-(chloromethyl)-1H-1,2,4-triazole-3-carboxylic acid (solidified foam);

with the use of 75.0 g (0.25 mole) of 2-amino-5-chloro-2'-(trifluoromethyl)-benzophenone: 1-[2-($\alpha,\alpha,\alpha$-trifluoro-o-tolyl)-4-chlorophenyl]-5-(chloromethyl)-1H-1,2,4-triazole-3-carboxylic acid;

with the use of 53.8 g (0.25 mole) of 2-amino-5-fluorobenzophenone: 1-(2-benzoyl-4-fluorophenyl)-5-(chloromethyl)-1H-1,2,4-triazole-3-carboxylic acid;

with the use of 69.0 g (0.25 mole) of 2-amino-5-bromobenzophenone: 1-(2-benzoyl-4-bromophenyl)-5-(chloromethyl)-1H-1,2,4-triazole-3-carboxylic acid.

(c) 33.2 g (0.20 mole) of potassium iodide is dissolved in 85 ml of water. The obtained solution is diluted with 850 ml of dioxane, and 71.5 g (0.175 mole) of 1-(2-benzoyl-4-chlorophenyl)-5-(chloromethyl)-1H-1,2,4-triazole-3-carboxylic acid [produced according to (b)] containing an equimolar amount of methanol added at 25° with stirring. The reaction solution is heated for one hour at 45°–50° and 0.5 liter of aqueous ammonia added; the mixture is heated for 2 hours at 45°–50° and concentrated in vacuo. The residue is dissolved in 2 liters of water and 2N hydrochloric acid added to the solution until an acid reaction to a congo-red indicator is obtained. The free carboxylic acid precipitates; it is filtered off under suction, washed neutral with water, afterwards washed with methanol, and dried in vacuo at 120°–130°. The obtained 6-phenyl-8-chloro-4H-s-triazolo[1,5-a] [1,4]benzodiazepine)-2-carboxylic acid decomposes at 170°.

The following are obtained in an analogous manner:
from 72.0 g (0.175 mole) of 1-[2-(o-chlorobenzoyl)-4-chlorophenyl]-5-(chloromethyl)-1H-1,2,4-triazole- 3-carboxylic acid:- 6-(o-chlorophenyl)-8-chloro-4H-s-triazolo [1,5-a][1,4]benzodiazepine-2-carboxylic acid, M.P. 190°–195° (decomposition; from methanol);

from 69.0 g (0.175 mole) of 1-[2-(o-fluorobenzoyl)-4-chlorophenyl]-5-(chloromethyl)-1H-1,2,4-triazole-3-carboxylic acid:- 6-(o-fluorophenyl)-8-chloro-4H-s-triazolo[1,5-a] [1,4]benzodiazepine-2-carboxylic acid, M.P. 179°–182° (decomposition; from methanol);

from 77.6 g (0.175 mole) of 1-[2-(α,α,α-trifluoro-o-tolyl)-4-chlorophenyl]-5-(chloromethyl)-1H-1,2,4-triazole-3-carboxylic acid:- 6-(α,α,α-trifluoro-o-tolyl)-8-chloro-4H-s-triazolo[1,5-a][1,4]benzodiazepine-2-carboxylic acid;

from 63.0 g (0.175 mole) of 1-(2-benzoyl-4-fluorophenyl)-5-(chloromethyl)-1H-1,2,4-triazole-3-carboxylic acid: 6-phenyl-8-fluoro-4H-s-triazole[1,5-a][1,4]benzodiazepine-2-carboxylic acid;

from 73.7 g (0.175 mole) of 1-(2-benzoyl-4-bromophenyl)-5-(chloromethyl)-1H-1,2,4-triazole-3-carboxylic acid: 6-phenyl-8-bromo-4H-s-triazolo[1,5-a] [1,4]benzodiazepine-2-carboxylic acid.

EXAMPLE 2

An amount of 3.63 g (0.010 mole) of 6-(o-fluorophenyl)-8-chloro-4H-s-triazolo[1,5-a][1,4]benzodiazepine-2-carboxylic acid is refluxed with 60 ml of thionyl chloride for 2 hours. The clear yellow solution is concentrated at 40° in vacuo and, to effect the total removal of thionyl chloride, the residue dissolved in 50 ml of abs. toluene and again concentrated by evaporation to obtain as residue crude 6-(o-fluorophenyl)-8-chloro-4H-s-triazolo[1,5-a][1,4]benzodiazepine-2-carbonyl chloride. It can be optionally recrystallised from dioxane and has then a M.P. of 196°–198° (decomposition).

For the further reaction, the whole of the above obtained crude acid chloride is dissolved in 55 ml of dioxane, and the solution of 5.10 g (0.050 mMole) of 1-methylpiperazine in 5 ml of dioxane added. The mixture is stirred for 3 hours at room temperature; it is then poured on ice-water containing 20 ml of 1N sodium carbonate solution, and extracted three times with methylene chloride. The organic phase is washed twice with saturated sodium chloride solution, dried over sodium sulphate, and then concentrated to dryness in vacuo. The resulting crude 1[[6-(o-fluorophenyl)-8-chloro-4H-s-triazolo[1,5-a][1,4]benzodiazepin-2-yl]-carbonyl]-4-methyl-piperazine is dissolved in a little ethanol, and alkanolic hydrogen chloride solution added until the pH-value of a sample is 3. The solution is cooled with an ice/sodium chloride mixture, ether is added and the hydrochloride caused to crystallise by trituration. The crystals are filtered off and dried in vacuo. The obtained 1-[[6-(o-fluorophenyl)-8-chloro-4H-s-triazolo[1,5-a][1,4]benzodiazepin-2-yl]-carbonyl]-4-methyl-piperazine hydrochloride melts at 190°–195°.

The carboxylic acid required as starting material is produced according to Example 1(a), (b) and (c), or in the following manner:

(a) A solution of 78.6 g (0.315 mole) of 2-amino-5-chloro-2'-fluorobenzophenone [cp. L. H. Sternback et al., J. Org. Chem. 26, 3781–3788, (1962)] in 394 ml of glacial acetic acid/conc. hydrochloric acid (4:1) is diazotised at room temperature, with stirring, with 63 ml (0.315 mole) of aqueous sodium nitrite solution. To the obtained diazonium salt solution there are added 240 g of ice and rapidly dropwise a solution of 79.0 g (0.315 mole) of (2-chloroacetamido)-malonic acid diethyl ester [cp. Ajay Kumar Bose, J. Indian Chem. Soc. 31, 108–110 (1954)] in 900 ml of acetone. A solution of 433.0 g (3.14 moles) of potassium carbonate in 770 ml of water is subsequently added dropwise within 60 minutes; stirring is maintained for a further hour, and ether and saturated sodium chloride solution then added. The ether solution is separated, washed with saturated sodium chloride solution, dried over sodium sulphate, and concentrated by evaporation. The solid residue is dissolved in the minimum amount of methylene chloride; hot hexane is added until clouding commences, and crystallisation induced by cooling and inoculation. The obtained (2-chloroacetamido)-[2-(o-fluorobenzoyl)-4-chlorophenylazo]-malonic acid diethyl ester melts at 98°–100°.

(b) A solution of 8.0 g (0.20 mole) of sodium hydroxide in 400 ml of water is added dropwise, in the course of 2 hours, to a solution of 51.2 g (0.10 mole) of [2-(o-fluorobenzoyl)-4-chlorophenylazo]-(2-chloroacetamido)-malonic acid diethyl ester in 600 ml of dioxane. The temperature of the reaction mixture rises during the addition from initially 20° to at most 30°, and the pH attains a value at the end of 8.5 to 9.0. The mixture is stirred for a further 45 minutes at room temperature, thereupon neutralised by the addition of glacial acetic acid, and concentrated in vacuo. Ice and 5% sodium bicarbonate solution are added to the residue; the mixture is extracted by shaking twice with ether, and the aqueous phase is retained. The organic phases are combined, washed with ice-cold 5% sodium bicarbonate solution and water, dried over sodium sulphate and concentrated in vacuo. The residue is recrystallised from isopropanol. After drying, the obtained 1-[2-(o-fluorobenzoyl)-4-chlorophenyl]-5-(chloromethyl)-1H-1,2,4-triazole-3-carboxylic acid ethyl ester melts at 97°–98°.

(c) A solution of 8.44 g (0.02 mole) of 1-[2-(o-fluorobenzoyl)-4-chlorophenyl]-5-(chloromethyl)-1H-1,2,4-triazole-3-carboxylic acid ethyl ester and 5.6 g (0.04 mole) of hexamethylenetetramine in 140 ml of abs. ethanol is refluxed for 6 hours. The solution is then concentrated at 40° in vacuo, 400 ml of ice-water added to the residue and extraction performed with methylene chloride. The organic phase is washed twice with ice-cold 1N hydrochloric acid and three times with water; it is then dried over sodium sulphate and concentrated in vacuo. The residue is recrystallised from isopropanol. After drying, the obtained 6-(o-fluorophenyl)-8-chloro-4H-s-triazolo[1,5-a] [1,4]benzodiazepine-2-carboxylic acid ethyl ester melts at 177°–179°.

(d) An amount of 4.81 g (0.0125 mole) of 6-(o-fluorophenyl)-8-chloro-4H-s-triazolo[1,5-a][1,4]benzodiazepine-2-carboxylic acid ether ester is refluxed in 250 ml of methanol and 25.5 ml (0.0255 mole) of 1N sodium hydroxide solution for 30 minutes. The reaction solution is subsequently concentrated by evaporation; the residue is dissolved in 50 ml of water, and 2N hydrochloric acid added until an acid reaction to a congo-red indicator is obtained. The precipitated carboxylic acid is filtered off under suction and washed with water until neutral. It is subsequently washed three times with 50 ml of methanol each time, and dried in vacuo at 100°. The obtained 6-(o-fluorophenyl)-8-chloro-4H-s-triazolo[1,5-s][1,4]benzodiazepine-2-carboxylic acid decomposes at 179°–182°.

EXAMPLE 3

The crude acid chloride is produced, analogously to Example 1, from 5.58 g (0.015 mole) of 6-phenyl-8-(trifluoromethyl)-4H-s-triazolo[1,5-a][1,4]benzodiazepine-2-carboxylic acid and 50 ml of thionyl chloride, and reacted with 100 ml of a 20% solution of dimethylamine in abs. dioxane. After processing analogously to Example 1, there is obtained N,N-dimethyl-6-phenyl-8-(trifluoromethyl)-4H-s-triazolo[1,5-a][1,4]benzodiazepine-2-carboxamide, M.P. 195°-197° (from ether).

There is obtained in an analogous manner, with 22 g (0.3 mole) of diethylamine in 100 ml of abs. dioxane, N,N-diethyl-6-phenyl-8-(trifluoromethyl)-4H-s-triazolo[1,5-a][1,4-benzodiazepine-2-carboxamide.

The carboxylic acid required as starting material is produced fully analogously to Example 2(a) – (d):

(a) From 83.5 g (0.315 mole) of 2-amino-5-(trifluoromethyl)-benzophenone there is obtained (2-chloroacetamido)-(2-benzoyl-α,α,α-trifluoro-p-tolylazo)-malonic acid diethyl ester in the form of red oil, which is further processed without purification.

(b) From 53.0 g (0.10 mole) of the ester produced according to (a) there is obtained 1-(2-benzoyl-α,α,α-trifluoro-p-tolyl)-5-(chloromethyl)-1H-1,2,4-triazole-3-carboxylic acid ethyl ester, M.P. 110°-111° (from ether/petroleum ether).

(c) From 8.76 g (0.02 mole) of the ester of (b) there is obtained 6-phenyl-8-(trifluoromethyl)-4-H-s-triazolo[1,5-a][1,4-benzodiazepine-2-carboxylic acid ethyl ester, M.P. 162°-164° (from abs. ethanol).

(d) Hydrolysis of 5.0 g (0.0125 mole) of the ester of (c) yields 6-phenyl-8-(trifluoromethyl)-4H-s-triazolo[1,5-a][1,4benzodiazepine-2-carboxylic acid, which decomposes at 195°.

EXAMPLE 4

Analogously to Example 1, the crude acid chloride is produced from 2.4 g (0.0069 mole) of 6-phenyl-8-nitro-4-H-s-triazolo[1,5-a][1,4]benzodiazepine-2-carboxylic acid and 50 ml of thionyl chloride. The obtained crude acid chloride is reacted with 50 ml of a 20% solution of dimethylamine in abs. dioxane, whereby there is obtained, analogously to Example 1, N,N-dimethyl-6-phenyl-8-nitro-4-H-s-triazolo[1,5-a][1,4]benzodiazepine-2-carboxamide, M.P. 209°-211° (from ethyl acetate)—

There is obtained in an analogous manner, with use of 50 ml of a 20% solution of diethylamine in dioxane: N,N-diethyl-6-phenyl-8-nitro-4H-s-triazolo[1,5-a][1,4]benzodiazepine-2-carboxamide.

There are obtained likewise analogously, starting with 2.5 g (0.0068 mole) of 6-(o-fluorophenyl)-8-nitro-4H-s-triazolo[1,5-a][1,4]benzodiazepine-2-carboxylic acid, 50 ml of thionyl chloride, and 50 ml of a 20% solution of dimethylamine in abs. dioxane and 50 ml of a 20% solution of diethylamine in abs. dioxane, respectively: N,N-dimethyl-6-(o-fluorophenyl)-8-nitro-4H-s-triazolo [1,5-a][1,4]benzodiazepine-2-carboxamide, M.P. 178°-180° (from ethyl acetate) and N,N-diethyl-6-(o-fluorophenyl)-8-nitro-4H-s-triazolo[1,5-a][1,4]benzodiazepine-2-carboxamide.

The carboxylic acids required as starting materials are produced as follows:

(a) A solution of 20 g (0.826 mole) of 2-amino-5-nitrobenzophenone (cp. Ullmann, Ber. 31, 1965) in 400 ml of glacial acetic acid and 20 ml of conc. hydrochloric acid is diazotised at 20°-25°, with stirring, with 16.5 ml (0.826 mole) of aqueous sodium nitrite solution. To the obtained diazonium salt solution there are added 400 g of ice, and rapidly dropwise a solution of 17.4 g (0.69 mole) of (2-chloroacetamido)-malonic acid diethyl ester [cp. Ajay Kumar Bose, J. Indian Chem. Soc. 31, 108–110 (1954)] in 400 ml of acetone. A solution of 114 g (0.826 mole) of potassium carbonate in 250 ml of water is subsequently added dropwise at 5°-10° within 20 minutes; stirring is continued for an hour, and benzene and saturated sodium chloride solution added. The benzene solution is separated, washed repeatedly with a mixture of saturated sodium chloride solution and 5% sodium bicarbonate solution until free from acid, dried over sodium sulphate and concentrated by evaporation, whereby crude (2-chloroacetamido)(2-benzoyl-4-hitrophenylazo)-malonic acid diethyl ester is obtained.

There is obtained in an analogous manner, with the use of 21.5 g (0.0826 mole) of 2-amino-5-nitro-2'-fluorobenzophenone (cp. Dutch Patent Application No. 64.05644 CA 62, 16137 f, and French Pat. No. 1,403,125), the crude (2-chloroacetamido)-[2-(o-fluorobenzoyl)-4-nitrophenylazo]malonic acid diethyl ester.

(b) 310 ml (0.155 mole) of 0.5N sodium hydroxide solution is added dropwise, in the course of two hours, to a solution of 42 g (0.082 mole) of (2-chloroacetamido)(2-benzoyl-4-nitrophenylazo)-malonic acid diethyl ester in 1 liter of dioxane, the temperature being maintained at 17°-20° by cooling. The pH-value finally is 8.0–8.5. The mixture is stirred for a further 30 minutes at 17°-20°; it is then neutralised by an addition of glacial acetic acid, and concentrated in vacuo to ca. 300 ml. Ice and 5% sodium bicarbonate solution are added to the concentrate and extraction performed twice with ethyl acetate. The organic phases are combined, washed with ice-cold 5% sodium bicarbonate solution and water, dried over sodium sulphate and concentrated in vacuo. An amount of 250 ml of ether is added to the residue, whereupon crystallisation occurs. Recrystallisation from benzene/ether then yields 1-(2-benzoyl-4-nitrophenyl)-5-(chloromethyl)-1H-1,2,4-triazole-3-carboxylic acid ethyl ester, M.P. 151°-152°.

There is obtained in an analogous manner, starting with 43.5 g (0.082 mole) of (2-chloroacetamido)-[2-(o-fluorobenzoyl)-4-nitrophenylazo]-malonic acid diethyl ester: 1-[2-(o-fluorobenzoyl)-4-nitrophenyl]-5-(chloromethyl)1H-1,2,4-triazole-3-carboxylic acid ethyl ester, M.P. 160°-162° (from benzene).

(c) A solution of 11.8 g (0.0285 mole) of the ester described in the first para. of (b) and 12 g (0.0855 mole) of hexamethylenetetramine in 750 ml of abs. ethanol is refluxed for 6 hours. The solution is then concentrated at 40° in vacuo; an amount of 500 ml of glacial acetic acid is added to the residue and the whole extracted twice with methylene chloride. The organic phase is washed twice with ice-cold 1N hydrochloric acid and three times with water, dried over sodium sulphate and concentrated in vacuo. The residue is recrystallised from ethanol. After drying in vacuo, the obtained 6-phenyl-8-nitro-4H-s-triazolo[1,5-a][1,4] benzodiazepine-2-carboxylic acid ethyl ester melts at 145°-147°.

In an analogous manner, 12.3 g (0.0285 mole) of the ester described in the second para. of (b) is reacted with 12 g of hexamethylenetetramine to give 6-(o-fluorophenyl)-8-nitro-4H-s-triazolo[1,5-a][1,4]benzodiazepine-2-carboxylic acid ethyl ester, M.P. 165°-167° (from ethanol).

(d) A solution of 1 ml (0.01 mole) of conc. sodium hydroxide solution (40%) in 50 ml of methanol is added to a solution of 2.85 g (0.0075 mole) of the ester described in the first para. of (c). The whole is allowed to stand for 30 minutes at room temperature; it is then acidified by the addition of 10 ml of 1N hydrochloric acid and concentrated in vacuo. The residue is repeatedly washed with water, and afterwards dried at 80°–100° in vacuo. The obtained 6-phenyl-8-nitro-4H-s-triazolo[1,5-a][1,4] benzodiazepine-2-carboxylic acid decomposes at 208°.

There is obtained in an analogous manner, from 3.0 g (0.0075 mole) of the ester described in the second para. of (c): 6-(o-fluorophenyl)-8-nitro-4H-s-triazolo[1,5-a][1,4] benzodiazepine-2-carboxylic acid, which decomposes at 190°.

EXAMPLE 5

An amount of 3.67 g (0.010 mole) of 6-phenyl-8-chloro-4H-s-triazolo[1,5-a][1,4]-benzodiazepine-2-carboxylic acid ethyl ester is dissolved at 40° in 300 ml of ethanol, and 50 ml of conc. aqueous ammonia solution is then added. The clear solution is allowed to stand for 24 hours at room temperature and thereupon concentrated at 40° in vacuo. The red residue is suspended in 100 ml of water, filtered under suction, and the filter residue subsequently washed with water. The resulting product is recrystallised from methanol and dried at 100°–120° in vacuo to obtain 6-phenyl-8-chloro-4H-s-triazolo[1,5-a][1,4]benzodiazepine-2-carboxamide, M.P. 252°–254°.

The following are obtained in an analogous manner:
with the use of 4.02 g (0.010 mole) of 6-(o-chlorophenyl)-8-chloro-4H-s-triazolo[1,5-a][1,4]benzodiazepine-2-carboxylic acid ethyl ester:- 6-(o-chlorophenyl)-8-chloro-4H-s-triazolo[1,5-a][1,4]benzodiazepine-2-carboxamide, M.P. 283°–285° (from methanol), and
with the use of 3.85 g (0.010 mole) of 6-(o-fluorophenyl)-8-chloro-4H-s-triazolo[1,5-a][1,4]benzodiazepine-2-carboxylic acid ethyl ester [cp. Example 2(a)–(c)]:- 6-(o-fluorophenyl)-8-chloro-4H-s-triazolo[1,5-a][1,4]benzodiazepine-2-carboxamide, M.P. 250°–252° (with decomposition, from ethanol);
with the use of 4.00 g (0.010 mole) of 6-phenyl-8-(trifluoromethyl)-4H-s-triazolo[1,5-a][1,4]benzodiazepine-2-carboxylic acid ethyl ester [cp. Example 3(a)–(c)]: 6-phenyl-8-(trifluoromethyl)-4H-s-triazolo[1,5-a][1,4]benzodiazepine-2-carboxamide; and
with the use of 3.77 g (0.010 mole) of 6-phenyl-8-nitro-4H-s-triazolo [1,5-a] [1,4] benzodiazepine-2-carboxylic acid ethyl ester [cp. Example 4(a)–(c)]:- 6-phenyl-8-nitro-4H-s-triazolo[1,5-a][1,4]benzodiazepine-2-carboxamide.

The first ethyl ester required as starting material is produced as follows:

(a) 6.77 g (0.020 mole) of 6-phenyl-8-chloro-4H-s-triazolo[1,5-a][1,4]benzodiazepine-2-carboxylic acid [cp. Example 1(a), (b) and (c)] is suspended in 250 ml of abs. ethanol. While being stirred and refluxed, the solution is saturated with hydrogen chloride gas. The obtained clear solution is refluxed for a further 10 hours, and afterwards concentrated at 40° in vacuo. The residue is dissolved in 100 ml of ice-cold 5% sodium bicarbonate solution and 100 ml of methylene chloride; the organic phase is separated, washed with water, dried over sodium sulphate and concentrated at 40° in vacuo. The crude greasy residue is refluxed for 1 hour with 100 ml of ether, whereby crystallisation occurs. After cooling to 0°, the crystals are filtered off under suction and washed with ether. 6-Phenyl-8-chloro-4H-s-triazolo[1,5-a][1,4]benzodiazepine-2-carboxylic acid ethyl ester, M.P. 137°–138°, is obtained.

The following is obtained analogously: starting with 7.46 g (0.020 mole) of 6-(o-chlorophenyl)-8-chloro-4H-s-triazolo[1,5-a][1,4]benzodiazepine-2-carboxylic acid: the ethyl ester thereof, M.P. 211°–213° (from ethanol).

EXAMPLE 6

An amount of 5.0 g (0.013 mole) of 6-(o-fluorophenyl)-8-chloro-4H-s-triazolo[1,5-a][1,4]benzodiazepine-2-carboxylic acid ethyl ester [cp. Example 2(a)–(c)] is dissolved, with heating, in 150 ml of methanol. There is then added to the still warm solution at 30°–40° a solution of 5.0 g (0.16 mole) of methylamine in 25 ml of methanol, and the whole stirred for 20 hours at room temperature. The reaction mixture is afterwards concentrated in vacuo to dryness; the residue is then dissolved in methylene chloride, and the opalescent solution filtered through a 2 cm thick layer of neutral aluminium oxide, activity I. Subsequent washing is performed with a large amount of methylene chloride, and the filtrate concentrated in vacuo to dryness. The residue is recrystallised from methylene chloride/hexane. After drying, the obtained N-methyl-6-(o-fluorophenyl)-8-chloro-4H-s-triazolo[1,5-a][1,4]benzodiazepine-2-carboxamide melts at 202°–203°.

The following are obtained in an analogous manner:
from 5.22 g (0.013 mole) of 6-(o-chlorophenyl)-8-chloro-4H-s-triazolo[1,5-a][1,4]benzodiazepine-2-carboxylic acid ethyl ester (cp. Example 5(a): N-methyl-6-(o-chlorophenyl)-8-chloro-4H-s-triazolo[1,5-a][1,4]benzodiazepine-2-carboxamide, M.P. 211°–213° (from isopropanol);
from 5.20 g (0.013 mole) of 6-phenyl-8-(trifluoromethyl)-4H-s-triazolo[1,5-a][1,4]benzodiazepine-2-carboxylic acid ethyl ester [cp. Example 3(a)–(c)]:- N-methyl-6-phenyl-8-(trifluoromethyl)-4H-s-triazolo[1,5-a][1,4]benzodiazepine-2-carboxamide; and
from 4.90 g (0.013 mole) of 6-phenyl-8-nitro-4H-s-triazolo[1,5-a][1,4]benzodiazepine-2-carboxylic acid ethyl ester [cp. Example 4(a)–(c)]: N-methyl-6-phenyl-8-nitro-4H-s-triazolo[1,5-a][1,4]benzodiazepine-2-carboxamide.

EXAMPLE 7

Pure gaseous dimethylamine free, in particular, from methylamine, is fed for 2 hours at room temperature, with stirring, into a suspension of 3.85 (0.01 mole) of 6-(o-fluorophenyl)-8-chloro-4H-s-triazolo[1,5-a][1,4]benzodiazepine-2-carboxylic acid ethyl ester [cp. Example 2(a)–(c)] in 200 ml of methanol. The clear reaction mixture is concentrated in vacuo to dryness. After recrystallisation from isopropanol, the residue yields pure N,N-dimethyl-6-(o-fluorophenyl)-8-chloro-4H-s-triazolo[1,5-a][1,4]benzodiazepine-2-carboxamide, M.P. 180°–182°.

The following final materials are obtained in an analogous manner by reaction with the below given amines in place of dimethylamine under the given reaction conditions:
with ethylamine, which is fed through as gas for 4 hours at 50°, there is obtained N-ethyl-6-(o-fluorophenyl)-8-chloro-4H-s-triazolo[1,5-a][1,4]benzodiazepine-2-carboxamide, M.P. 232°–234° (from isopropanol);

with 19 g (0.32 mole) of isopropylamine during 4 hours at 60° there is obtained N-isopropyl-6-(o-fluorophenyl)-8-chloro-4H-s-triazolo[1,5-a][1,4]benzodiazepine-2-carboxamide, M.P. 255°–258° (from isopropanol);

with 2.1 g (0.034 mole) of 2-aminoethanol during 3 hours at 65° there is obtained N-(2-hydroxyethyl)-6-(o-fluorophenyl)-8-chloro-4H-s-triazolo[1,5-a][1,4]benzodiazepine-2-carboxamide, M.P. 236°–240° (decomposition, from isopropanol);

with 10.0 g (0.15 mole) of morpholine during 16 hours at 65° there is obtained 4-[[6-(o-fluorophenyl)-8-chloro-4H-s-triazolo[1,5-a][1,4]benzodiazepin-2-yl]-carbonyl]-morpholine, M.P. 180°–182° (from isopropanol);

with 2.1 g (0.0295 mole) of pyrrolidine during 3 hours at 65° there is obtained 1-[[6-(fluorophenyl)-8-chloro-4H-s-triazolo[1,5-a][1,4]benzodiazepin-2-yl]-carbonyl]-pyrrolidine, M.P. 202°–204° (from isopropanol);

with 3.5 g (0.04 mole) of piperidine during 12 hours at 65° there is obtained 1-[[6-(o-fluorophenyl)-8-chloro-4H-s-triazolo[1,5-a][1,4]benzodiazepin-2-yl]-carbonyl]-piperidine, which liquifies at 100°–105°;

with 4.63 g (0.045 mole) of N,N-dimethyl-1,3-propanediamine during 6 hours at 65°, and treatment of the crude product with ethanolic hydrogen chloride solution, there is obtained N-[3-(dimethylamino)-propyl]-6-(o-fluorophenyl)-8-chloro-4H-s-triazolo[1,5-a][1,4]benzodiazepine-2-carboxamide hydrochloride, M.P. 160°–165° (from ethanol/ethyl acetate);

with 5.22 g (0.045 mole) of N,N-diethyl-ethylenediamine during 6 hours at 65°, and treatment of the crude product with ethanolic hydrogen chloride solution, there is obtained N-[2-(diethylamino)-ethyl]-6-(o-fluorophenyl)-8-chloro-4H-s-triazolo[1,5-a][1,4]benzodiazepine-2-carboxamide hydrochloride.

EXAMPLE 8

An amount of 3.0 ml (0.042 mole) of conc. ammonia is added to a solution of 2.56 g (0.005 mole) of (2-chloroacetamido)-[2-(o-fluorobenzoyl)-4-chlorophenylazo]-malonic acid diethyl ester [cp. Example 2(a)] in 10 ml of dimethylformamide at room temperature. The mixture is stirred for 16 hours at room temperature, and subsequently heated for 6 hours at 70°. It is thereupon poured on 100 ml of ice water and extracted three times with ethyl acetate. The organic extracts are washed with water and with saturated sodium chloride solution, dried over sodium sulphate and concentrated in vacuo to dryness. The residue is dissolved in methylene chloride/methanol (94:6) and the solution chromatographed on 100 g of silica gel. Methylene chloride/methanol (94:6) is used as the elution agent. The fractions containing the crude product [$R_f$-value: 0.5 in the system methylene chloride/methanol (95:5)] are combined, and recrystallised from ethanol/methylene chloride. After drying, the obtained 6-(o-fluorophenyl)-8-chloro-4H-s-triazolo[1,5-a][1,4]benzodiazepine-2-carboxamide melts at 250°–252° with decomposition.

EXAMPLE 9

An amount of 1.99 g (0.012 mole) of potassium iodide is dissolved in 6 ml of water. The obtained solution is diluted with 20 ml of dioxane; an addition is then made at 25°, with stirring, of a solution of 4.3 g (0.01 mole) of N,N-diethyl-1-(2-benzoyl-4-chlorophenyl)-5-(chloromethyl)-1H-1,2,4-triazole-3-carboxamide in 40 ml of dioxane, and the reaction solution heated for 1 hour at 50°. There is then added 35 ml of conc. aqueous ammonia solution, the mixture heated for a further 2 hours at 50°, and subsequently concentrated in vacuo. Water is added to the residue and extraction performed twice with methylene chloride. The organic phase is washed with water and saturated sodium chloride solution; it is then dried over sodium sulphate and concentrated in vacuo to dryness. The residue is recrystallised from benzene/cyclohexane to obtain pure N,N-diethyl-6-phenyl-8-chloro-4H-s-triazolo[1,5-a][1,4]benzodiazepine-2-carboxamide, M.P. 175°–177°.

The following are obtained in an analogous manner: starting with 4.65 g (0.01 mole) of N,N-diethyl-1-[2-(o-chlorobenzoyl)-4-chlorophenyl]-5-(chloromethyl)-1H-1,2,4-triazole-3-carboxamide:-N,N-diethyl-6-(o-chlorophenyl)-8-chloro-4H-s-triazolo[1,5-a][1,4]benzodiazepine-2-carboxamide, M.P. 156°–158° (from isopropanol), and starting with 4.2 g (0.01 mole) of N,N-dimethyl-1-[2-(o-fluorobenzoyl)-4-chlorophenyl]-5-(chloromethyl)-1H-1,2,4-triazole-3-carboxamide:-N,N-dimethyl-6-(o-fluorophenyl)-8-chloro-4H-s-triazolo[1,5-a][1,4]benzodiazepine-2-carboxamide, M.P. 180°–182° (from isopropanol).

The starting materials are produced as follows:

(a) An amount of 60 ml of oxalyl chloride is poured over 11.7 g (0.031 mole) of 1-(2-benzoyl-4-chlorophenyl)-5-(chloromethyl)-1H-1,2,4-triazole-3-carboxylic acid [cp. Example 1 (a) and (b)] and the whole refluxed for 1 hour. The clear yellow solution is concentrated at 40° in vacuo and an addition then made to the residue, to effect the total removal of oxalyl chloride, of 100 ml of benzene, and the solution again concentrated by evaporation.

The obtained crude 1-(2-benzoyl-4-chlorophenyl)-5-(chloromethyl)-1H-1,2,4-triazole-3-carbonyl chloride is dissolved in 400 ml of dioxane, and a solution of 4.55 g (0.062 mole) of diethylamine in 100 ml of dioxane added dropwise at room temperature within 90 minutes. The dietylamine hydrochloride gradually precipitates out. The reaction mixture is concentrated in vacuo to dryness. Ice-water and ether are added to the residue; the organic phase is separated, and washed successively with cold 1N hydrochloric acid, with cold 1N sodium hydroxide solution and with saturated sodium chloride solution. After drying over sodium sulphate and concentration in vacuo, there is obtained crude N,N-diethyl-1-(2-benzoyl-4-chlorophenyl)-5-(chloromethyl)-1H-1,2,4-triazole-3-carboxamide, which, after recrystallisation from isopropanol, melts at 118°–119°.

The following are obtained in an analogous manner:
with the use of 12.8 g (0.031 mole) of 1-[2-(o-chlorobenzoyl)-4-chlorophenyl]-5-(chloromethyl)-1H-1,2,4-triazole-3-carboxylic acid and 4.55 g (0.062 mole) of diethylamine: N,N-diethyl-1-[2-(o-chlorobenzoyl)-4-chlorophenyl]-5-(chloromethyl)-1H-1,2,4-triazole-3-carboxamide, and
with the use of 12.26 g (0.031 mole) of 1-[2-(o-fluorobenzoyl)-4-chlorophenyl]-5-(chloromethyl)-1H-1,2,4-triazole-3-carboxylic acid and 2.8 g (0.062 mole) of dimethylamine: N,N-dimethyl-1-[2-(o-fluorobenzoyl)-4-chlorophenyl]-5-(chloromethyl)-1H-1,2,4-triazole-3-carboxamide.

EXAMPLE 10

A solution of 4.31 g (0.01 mole) of N,N-diethyl-1-(2-benzoyl-4-chlorophenyl)-5-(chloromethyl)-1H-1,2,4-triazole-3-carboxamide [cp. Examples 1 (a) and (b) and 9 (a)] and 2.80 g (0.02 mole) of hexamethylenetetramine in 120 ml of ethanol is refluxed for 10 hours. The solution is then concentrated at 40° in vacuo; 100 ml of ice water is added to the residue and extraction performed twice with methylene chloride. The organic phase is washed twice with cold 1N hydrochloric acid and twice with water, dried over sodium sulphate and concentrated in vacuo. The residue is recrystallised from benzenecyclohexane, whereupon the obtained pure N,N-diethyl-6-phenyl-8-chloro-4H-s-triazolo[1,5-a][1,4]benzodiazepine-2-carboxamide melts at 175°–177°.

There is obtained in an analous manner, starting with 2.32 g (0.005 mole) of N,N-diethyl-1-[2-(o-chlorobenzoyl)-4-chlorophenyl]-5-(chloromethyl)-1H-1,2,4-triazole-3-carboxamide [cp. Examples 1 (a) and (b) and 9 (a)], N,N-diethyl-6-(o-chlorophenyl)-8-chloro-4H-s-triazolo [1,5-a]]1,4]benzodiazepine-2-carboxamide, M.P. 156°–158° (isopropanol); and, starting with 2.1 g (0.005 mole) of N,N-dimethyl-1-[2-(o-fluorobenzoyl)-4-chlorophenyl]-5-(chloromethyl)-1H-1,2,4-triazole-3-carboxamide [cp. Examples 1 (a) and (b) and 9 (a)], N,N-dimethyl-6-(o-fluorophenyl)-8-chloro-4H-s-triazolo [1,5-a][1,4]benzodiazepine-2-carboxamide, M.P. 180°–182° (from isopropanol).

EXAMPLE 11

An amount of 1.05 g (0.021 mole) of hydrazine hydrate is added to a solution of 5.41 g (0.01 mole) of N,N-diethyl-1-(2-benzoyl-4-chlorophenyl)-5-(phthalimidomethyl)-1H-1,2,4-triazole-3-carboxamide in 150 ml of ethanol, and the reaction mixture stirred for 16 hours at room temperature and for a further 5 hours at 60°. The formed phthalic acid hydrazide is then filtered off, and the filtrate concentrated in vacuo to dryness. Ice water is added to the residue, and extraction performed twice with ethyl acetate. The organic phase is washed twice with ice cold 1N sodium hydroxide solution, once with ice cold 1N hydrochloric acid solution, and twice with water. After drying of the solution over sodium sulphate, the solvent is evaporated off in vacuo. After recrystallisation from benzene/cyclohexane, the residue yields N,N-diethyl-6-phenyl-8-chloro-4H-s-triazolo[1,5-a][1,4]benzodiazepine-2-carboxamide, M.P. 175°–177°.

The following are obtained in an analous manner:
from 5.75 g (0.01 mole) of N,N-diethyl-1-[2-(o-chlorobenzoyl)-4-chlorophenyl]-5-(phthalimidomethyl)-1H-1,2,4-triazole-3-carboxamide: N,N-diethyl-6-(o-chlorophenyl)-8-chloro-4H-s-triazolo[1,5-a][1,4]benzodiazepine-2-carboxamide, M.P. 156°–158° (from isopropanol); and,
starting with 4.31 g (0.01 mole) of N,N-dimethyl-1-[2-(o-fluorobenzoyl)-4-chlorophenyl]-5-(ph thalimidomethyl)- 1H-1,2,4-triazole-3-carboxamide:- N,N-dimethyl-6-(o-fluorophenyl)-8-chloro-4H-s-triazolo[1,5-a][1,4]benzodiazepine-2-carboxamide, M.P. 180°–182° (from isopropanol).

The starting materials are produced as follows:

(a) A solution of 8.62 g (0.02 mole) of N,N-diethyl-1-(2-benzoyl-4-chlorophenyl)-5-(chloromethyl)-1 H-1,2,4-triazole-3-carboxamide [cp. Examples 1 (a) and (b) and 9 (a)] and 4.63 g (0.025 mole) of potassium phthalimide in 200 ml of dimethylformamide is stirred for 2 hours at 50°. The reaction mixture is thereupon poured on ice water and extracted twice with ethyl acetate. The organic phase is washed twice with water, dried over sodium sulphate, and concentrated in vacuo to dryness. The residue is dissolved in ethyl acetate, and the solution chromatographed on 500 g of silica gel. Ethyl acetate is used as the elution agent. The fractions containing the desired product are combined. There is thus obtained pure but amorphous N,N-diethyl-1-(2-benzoyl-4-chlorophenyl)-5-(phthalimidomethyl)-1H-1,2,4-triazole-3-carboxamide, which liquifies at 85°-90°.

The following are obtained in an analogous manner:
starting with 9.13 g (0.02 mole) of N,N-diethyl-1-[2-(o-chlorobenzoyl)-4-chlorophenyl]-5-(chloromethyl)-1H-1,2,4-triazole-3-carboxamide [cp. Examples 1 (a) and (b) and 9 (a)]: N,N-diethyl-1-[2-(o-chlorobenzoyl)-4-chlorophenyl]-5-(phthalimidomethyl)-1H-1,2,4,-triazole-3-carboxamide; and,
starting with 8.98 g (0.02 mole) of N,N-dimethyl-1[2-(o-fluorobenzoyl)-4-chlorophenyl]-5-(chloromethyl)-1H-1,2,4-triazole-3-carboxamide [cp. Examples 1 (a) and (b) and 9 (a)]: N,N-dimethyl-1-[2-(o-fluorobenzoyl)-4-chlorophenyl]-5-(phthalimidomethyl)-1H-1,2,4-triazole-3-carboxamide.

EXAMPLE 12

2.94 g (0.06 mole) of sodium cyanide is suspended in 100 ml of isopropanol, and 50 ml of a 20% solution of dimethylamine in dioxane added at 0°–5° to the suspension. After 10 minutes, a solution of 4 g (0.0124 mole) of 6-phenyl-8-chloro-4H-s-triazolo[1,5-a][1,4]benzodiazepine-2-carboxaldehyde in 50 ml of dioxane is quickly added dropwise, and, after a further 10 minutes, an addition made in two portions of 20.8 g of active manganese dioxide. The whole is stirred for a further 3 hours at 5°, filtered, and the filtrate concentrated in vacuo. After recrystallisation from methylene chloride/hexane, N,N-dimethyl-6-phenyl-8-chloro-4H-s-triazolo[1,5-a][1,4]benzodiazepine-2-carboxamide is obtained, M.P. 135°–137°.

The following are obtained in an analogous manner:
with the use of 4.22 g (0.0124 mole) of 6-(o-fluorophenyl)-8-chloro-4H-s-triazolo[1,5-a][1,4]benzodiazepine-2-carboxaldehyde: N,N-dimethyl-6-(o-fluorophenyl)-8-chloro-4H-s-triazolo[1,5-a][1,4]benzodiazepine-2-carboxamide, M.P. 180°–182° (from isopropanol); and,
with the use of 4.42 g (0.01 mole) of 6-(o-chlorophenyl)-8-chloro-4H-s-triazolo[1,5-a][1,4]benzodia-zepine-2-carboxaldehyde: N,N-dimethyl-6-(o-chloro-phenyl)-8-chloro-4H-s-triazolo[1,5- a][1,4]benzodiazepine-2-carboxamide, M.P. 142°–145° (from isopropanol).

The following are obtained, likewise analogously, by reaction of the following aldehydes with the given bases of the general formula III, or with solutions thereof:

From 4.00 g (0.0124 mole) of 6-phenyl-8-chloro-4H-s-triazolo[1,5-a][1,4]benzodiazepine-2-carboxaldehyde with 50 ml of saturated solution of ammonia in isopropanol: 6-phenyl-8-chloro-4H-s-triazolo[1,5-a][1,4]benzodiazeine-2-carboxamide, M.P. 252°–254° (from methanol),
  and with 50 ml of a 10% solution of methylamine in dioxane: N-methyl-6-phenyl-8-chloro-4H-s-triazolo[1,5-a][1,4]benzodiazepine-2-carboxamide;
  from 4.22 g (0.0124 mole) of 6-(o-fluorophenyl)-8-chloro-4H-s-triazolo[1,5-a][1,4]benzodiazepine-2-carboxaldehyde with the ame bases: 6-(o-fluorophenyl)-8-chloro-4H-s-triazolo[1,5-a][1,4]benzodiazepine-2-carboxamide, M.P. 250°–252° (from ethanol),
  or N-methyl-6-(o-fluorophenyl)-8-chloro-4H-s-triazolo [1,5-a][1,4]benzodiazepine-2-carboxamide, M.P. 202°–203° (from methylene chloride/ hexane);
  and from 4.42 g (0.0124 mole) of 6-(o-chlorophenyl)-8-chloro-4 H-s-triazolo[1,5-a][1,4]benzodiazepine-2-carboxaldehyde with the same bases: 6-(o-chlorophenyl)-8-chloro-4H-s-triazolo[1,5-a][1,4]benzodiazepine-2-carboxamide, M.P. 283°–285° (from methanol), or N-methyl-6-(o-chlorophenyl)-8-chloro-4H-s-triazolo [1,5-a][1,4]benzodiazepine-2-carboxamide, M.P. 211°–213° (from isopropanol).

The aldehydes required as starting materials are produced as follows:

(a) A mixture of 3.5 ml of a 3.47-molar benzene solution of sodium-bis-(ethoxymethoxy)-aluminium hydride and 30 ml of abs. toluene is added dropwise within 15 minutes at −70°, with stirring, to a solution of 1.84 g (0.005 mole) of 6-phenyl-8-chloro-4H-s-triazolo[1,5-a][b 1,4]benzodiazepine-2-carboxylic acid ethyl ester [see Example 5 (a)] in 30 ml of abs. toluene. Stirring is maintained for a further 30 minutes at −70°, and 10 ml of ethyl acetate saturated with water then slowly added dropwise. A dropwise addition of 25 ml of 2N sodium hydroxide solution is thereupon slowly made, with the temperature of the reaction mixture gradually rising to 20°. Extraction is performed three times with ethyl acetate; the organic phases are separated, and washed with ice cold 2N sodium hydroxide solution, with water and with saturated sodium chloride solution. After drying over sodium sulphate, the ethyl acetate solution is concentrated in vacuo, the residue dissolved in toluene/ethyl acetate (9:1), and the solution chromatographed on 60 g of silica gel, elution being effected with the same solvent mixture. The fractions containing the desired product are combined, concentrated by evaporation, and boiled up with ether, whereupon crystallisation occurs. After cooling to 0°, the crystals are filtered off under suction, and dried at 90° in vacuo. There is thus obtained 6-phenyl-8-chloro-4H-s-triazolo[1,5-a][1,4]benzodiazepine-2-carboxaldehyde, M.P. 165°–167°.

The following are obtained in an analogous manner:
  with the use of 1.93 g (0.005 mole) of 6-(o-fluorophenyl)-8-chloro-4H-s-triazolo[1,5-a][1,4]benzodiazepine-2-carboxylic acid ethyl ester [see Example 3(a)–(c)]: 6-(o-fluorophenyl)-8-chloro-4H-s-triazolo[1,5-a][1,4]benzodiazepine-2-carboxaldehyde; and,
  with the use of 2.01 g (0.005 mole) of 6-(o-chlorophenyl)-8-chloro-4H-s-triazolo[1,5-a][1,4]benzodiazepine-2-carboxylic acid ethyl ester [see Example 5(a)]: 6-(o-chlorophenyl)-8-chloro-4H-s-triazolo[1,5-a][1,4]benzodiazepine-2-carboxaldehyde.

The required aldehydes can be produced also by a two-stage reaction sequence:

(b) 11.0 g (0.030 mole) of 6-phenyl-8-chloro-4H-s-triazolo [1,5-a][1,4]benzodiazepine-2-carboxylic acid ethyl ester [cp. Example 5(a)] dissolved in 110 ml of abs. tetrahydrofuran is added dropwise within one hour, with ice cooling, to a suspension of 2.30 g (0.06 mole) of lithium aluminium hydride in 150 ml of abs. tetrahydrofuran. The mixture is stirred for a further 30 minutes at 0°–5°, and 11.5 ml of 1N sodium hydroxide solution then carefully added dropwise. The inorganic salts are filtered off. The filtrate is thereupon concentrated in vacuo, the residue dissolved in 200 ml of chloroform, washed with 1N sodium hydroxide solution and then with water. After drying over sodium sulphate, the chloroform solution is concentrated by evaporation in vacuo, and the residue recrystallised from isopropanol. After drying, the obtained 6-phenyl-8-chloro-4H-s-triazolo[1,5-a][1,4]benzodiazepine-2-methanol melts at 185°–186°.

The following are obtained in an analogous manner:
  with the use of 11.5 g (0.030 mole) of 6-(o-fluorophenyl)-8-chloro-4H-s-triazolo[1,5-a][1,4]-benzodiazepine-2-carboxylic acid ethyl ester: 6-(o-fluorophenyl)-8-chloro-4H-s-triazolo[1,5-a][1,4]benzodiazepine-2-methanol, M.P. 138°–145° (from isopropanol); and,
  with the use of 12.03 g (0.030 mole) of 6-(o-chlorophenyl)-8-chloro-4H-s-triazolo[1,5-a][1,4]benzodiazepine-2-carboxylic acid ethyl ester: 6-(o-chlorophenyl)-8-chloro-4H-s-triazolo[1,5-a][1,4]benzodiazepine-2-methanol.

(c) 11.0 g of active manganese dioxide is added to a solution of 4.0 g (0.0123 mole) of 6-phenyl-8-chloro-4H-s-triazolo [1,5-a][1,4]benzodiazepine-2-methanol in 400 ml of benzene, and the whole refluxed for 2 hours. The reaction mixture is thereupon filtered and the filtrate concentrated in vacuo. The residue is dissolved in benzene/ethyl acetate (9:1), and the solution chromatographed on 200 g of silica gel, with the same solvent mixture being used as the eluent. The fractions containing the desired product are combined, concentrated by evaporation, and boiled up with ether, whereby crystallisation occurs. After cooling to 0°, the crystals are filtered off under suction. After drying at 90° in vacuo, the obtained 6-phenyl-8-chloro-4H-s-triazolo[1,5-a][1,4]benzodiazepine-2-carboxaldehyde melts at 165°–167°.

The corresponding aldehydes are obtained analogously with the use of 4.22 g (0.0123 mole) of 6-(o-fluorophenyl)-8-chloro-4H-s-triazolo[1,5-a][1,4]-benzodiazepine-2-methanol and 4.42 g (0.0123 mole) of 6-(o-chlorophenyl)-8-chloro-4H-s-triazolo[1,5-a][1,4]benzodiazepine-2-methanol, respectively.

EXAMPLE 13

A solution of 6.1 g (0.035 mole) of 75% m-chloroperoxybenzoic acid in 140 ml of methylene chloride is added dropwise within 20 minutes at 0° to a solution of 6.8 g (0.018 mole) of N,N-dimethyl-6-(o-fluorophenyl)-8-chloro-4H-s-triazolo[1,5-a][1,4]benzodiazepine-2-carboxamide in 270 ml of methylene chloride. The clear reaction mixture is stirred for 3 hours at 0°–5°, and afterwards for 20 hours at room temperature. The reaction solution is then concentrated in vacuo to dryness; the residue is dissolved in a little methylene chloride, and ether added until a slight clouding occurs. The precipitated crystals are filtered off and recrystallised from methylene chloride/ether. After 20 hours drying at 100°/0.05 Torr, N,N-dimethyl- 6-(o-fluorophenyl)-8-chloro-4H-s-triazolo [1,5-a][1,4]benzodiazepine-2-carboxamide-5-oxide, M.P. 170°–172°, is obtained (with decomposition). The crystals contain ca. ½ mole of methylene chloride.

The 5-oxides of the further final products of Examples 1–12 can be produced in an analogous manner.

What we claim is:

1. A compound of the formula IV

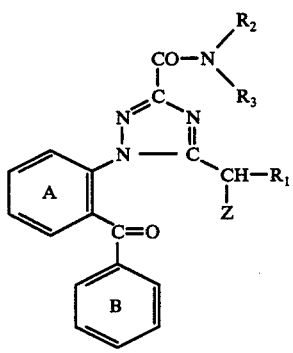

wherein

Z is hydroxy, chloro or iodo, $R_1$ represents hydrogen, or an alkyl group having 1 to 3 carbon atoms, and $R_2$ and $R_3$ independently of each other, represent hydrogen, alkyl groups having 1 to 6 carbon atoms, or hydroxyalkyl groups having in all 4 to 7 carbon atoms, or aralkyl groups having 7 to 9 carbon atoms, or together with the adjacent nitrogen atom, the 1-pyrrolidinyl-, piperidino-, 4-methyl-1-piperazinyl, or morpholino group;

wherein each of the rings A and B independently of the other, is unsubstituted or substituted by one member of the group consisting of halogen up to atomic number 35, trifluoromethyl or nitro groups, and its salts.

2. A compound of the formula V

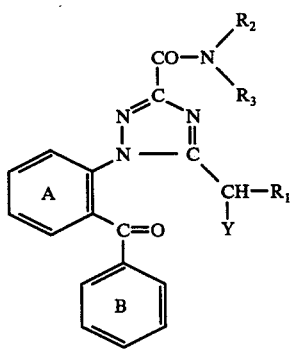

wherein

Y represents phthalimido, $R_1$ represents hydrogen, or an alkyl group having 1 to 3 carbon atoms, and $R_2$ and $R_3$ independently of each other, represent hydrogen, alkyl groups having 1 to 6 carbon atoms, or hydroxyalkyl groups having in all 4 to 7 carbon atoms, or aralkyl groups having 7 to 9 carbon atoms, or together with the adjacent nitrogen atom, the 1-pyrrolidinyl-, piperidino-, 4-methyl-1-piperazinyl, or morpholino group;

wherein each of the rings A and B independently of the other, is unsubstituted or substituted by one member of the group consisting of halogen up to atomic number 35, trifluoromethyl or nitro groups, and its salts.

3. A compound of the formula VI

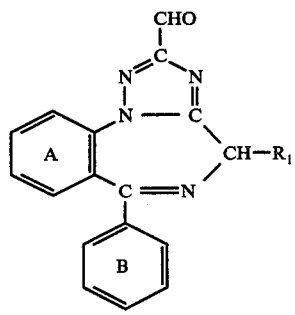

wherein $R_1$ represents hydrogen, or an alkyl group having 1 to 3 carbon atoms, and wherein each of the rings A and B independently of the other, is unsubstituted or substituted by one member of the group consisting of halogen up to atomic number 35, trifluoromethyl or nitro groups, its 5-oxide and its salts.

4. A compound according to claim 1 wherein Z is chloro or iodo.

5. A compound according to claim 1 wherein Z is chloro or iodo, $R_1$ represents hydrogen, $R_2$ and $R_3$ independently of each other represent hydrogen, methyl groups or ethyl groups, the ring A is substituted by chlorine, nitro, or trifluoromethyl and the ring B is unsubstituted or substituted in the o-position by fluorine or chlorine.

6. A compound according to claim 2 having the formula V given in claim 2, wherein Y represents the phthalimido group, $R_1$ represents hydrogen, $R_2$ and $R_3$ independently of each other represent hydrogen, methyl groups or ethyl groups, the ring A is substituted by chlorine, nitro or trifluoromethyl and the ring B is unsubstituted or substituted in the o-position by fluorine or chlorine.

7. A compound according to claim 3, having the formula VI given in claim 3, wherein $R_1$ represents hydrogen, the ring A is substituted by chlorine, the nitro group or the trifluoromethyl group in the 8-position and the ring B is unsubstituted or substituted in the o-position by fluorine or chlorine.

* * * * *